United States Patent [19]

Hromatka et al.

[11] 4,028,373

[45] June 7, 1977

[54] THIOPHENE SACCHARINES

[75] Inventors: Otto Hromatka; Dieter Binder, both of Wien, Austria

[73] Assignee: BASF Aktiengesellschaft, Ludwigshafen (Rhine), Germany

[22] Filed: Sept. 2, 1975

[21] Appl. No.: 609,623

[30] Foreign Application Priority Data

Sept. 16, 1974 Austria .............................. 7448/74
Sept. 16, 1974 Austria .............................. 7449/74
Sept. 16, 1974 Austria .............................. 7450/74

[52] U.S. Cl. ............................ 260/301; 260/329 S
[51] Int. Cl.² ...................................... C07D 513/04

[58] Field of Search ................................... 260/301

[56] References Cited

UNITED STATES PATENTS 3,050,553  8/1962  Novello .............................. 260/301

*Primary Examiner*—Richard J. Gallagher
*Attorney, Agent, or Firm*—Keil, Thompson & Shurtleff

[57] ABSTRACT

Thiophene analogs of saccharine, i.e., the new compounds 2,3-dihydro-3-oxothieno-[3,4-d]-, -[2,3-d]- and -[3,2-d]-isothiazole-1,1-dioxide, and processes for their manufacture. The new compounds are excellent sweeteners and have no unpleasant taste.

8 Claims, No Drawings

THIOPHENE SACCHARINES

The present invention relates to new thiophene saccharine having excellent sweetening power, no unpleasant taste and being non-toxic, and processes for their manufacture.

Of the chemical compounds suitable as sweeteners, only a few are in effect used, and, of these few, none simultaneously fulfils the three requirements of high sweetening power, non-toxicity and absence of unpleasant taste.

In view of the increasing demand for sweeteners, the object of the invention was therefore to provide a sweetener meeting the said criteria.

This object was surprisingly achieved with compounds of the formulae

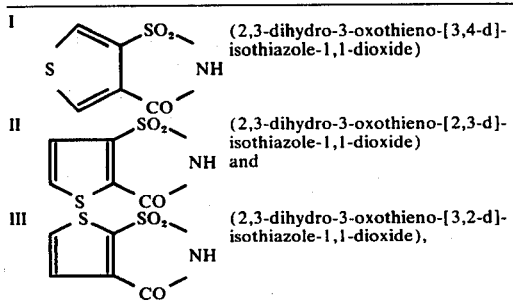

I (2,3-dihydro-3-oxothieno-[3,4-d]-isothiazole-1,1-dioxide)

II (2,3-dihydro-3-oxothieno-[2,3-d]-isothiazole-1,1-dioxide) and

III (2,3-dihydro-3-oxothieno-[3,2-d]-isothiazole-1,1-dioxide), and their non-toxic and water-soluble salts.

Of these compounds, I has the greatest sweeting power and is therefore preferred.

Suitable salts of the thieno-saccharines I to III are all non-toxic, i.e., physiologically unobjectionable, salts, particularly the alkali metal salts, such as the potassium and especially sodium salts, ammonium salts, and the alkaline earth metal salts, especially the calcium salt. Further suitable cations of the salts may if necessary be selected by the skilled worker as the cations — as stated above — must be non-toxic and water-soluble and these properties of certain cations of metals are well-known or, in the case of water solubility, can be determined by a simple experiment.

The starting materials for the preparation of the new compounds I to III are for instance the chloro- or bromothiophene carboxylic acids of the formula IV (in the case of III the starting material may also be 2,5-dichlorothiophene-3-dicarboxylic acid) in which the chlorine atom and the carboxylic groups are attached to adjacent carbon atoms; the subsequent reactions are carried out in accordance with the following formula scheme (in all formulae the substituents are attached to adjacent carbon atoms of the thiophene ring):

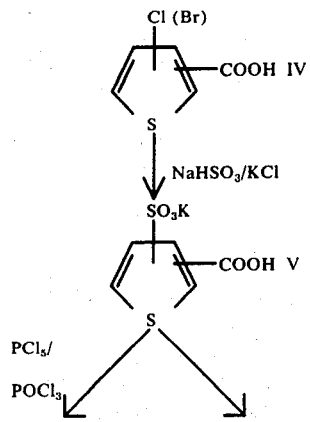

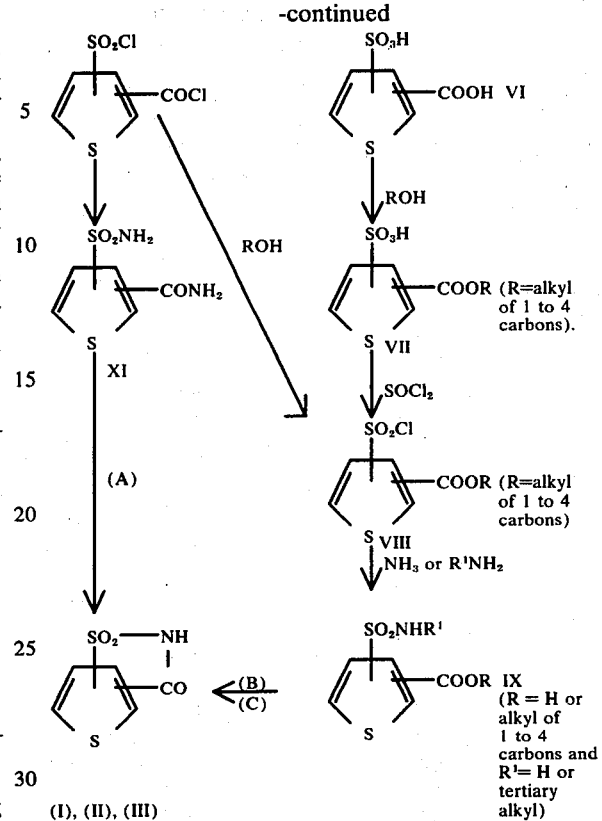

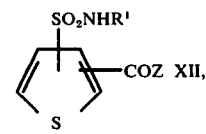

(I), (II), (III)

Reaction to the thiophene saccharines may be summarily described by the cyclization of compounds of the formula $$\text{SO}_2\text{NHR}^1$$
$$\text{COZ} \quad \text{XII,}$$

where the radicals SO$_2$NHR$^1$ and COZ are always attached to adjacent carbon atoms and Z denotes a readily eliminable functional group and in particular the radicals OH, NH$_2$ and OR, R denoting low molecular-weight alkyl, especially of 1 to 4 carbons, and R$^1$ denotes hydrogen or tertiary alkyl of, e.g., 4 to 13 carbons, especially tert-butyl, with the aid of condensing agents (examples of which are given below) and in the presence or absence of a solvent.

In route A the sulfamoyl thiophene carboxamide XI is prepared and directly cyclized to thiophene saccharine in the presence of condensation agents, such as alcoholic alkali metal alcoholate solution, at atmospheric or superatmospheric pressure, e.g. 1 to 10 atmospheres, and at temperatures of from 50° to 200° C, e.g., 120° C. Suitable condensing agents are alkali metal and alkaline earth metal hydrides, alkali metal amides and alkali metals. Examples of solvents are anhydrous inert solvents such as dimethylformamide, dimethyl sulfoxide, tri-dimethylaminophosphoryl amide, nitromethane, pyridine, and aliphatic and aromatic hydrocarbons, especially lower aliphatic alcohols.

In route B it is the sulfamoylthiophene carboxylate which is cyclized, advantageously by converting the esters of low-molecular-weight alcohols, e.g., of 1 to 4 carbons of the formula IX, i.e., 3-sulfamoylthiophene-4-carboxylate, 2-sulfamoylthiophene-3-carboxylate and 3-sulfamoylthiophene-2-carboylate into their anhydrous alkali metal or alkaline earth metal salts by means of alkali metal hydroxides; alkali metal alcoholates; alkaline earth metal alcoholates; alkali metal hydrides; alkaline earth metal hydrides; alkali metal amides; and alkali metals, or by converting the esters with a quaternary ammonium hydroxide, e.g., tetramethylammonium hydroxide, into the anhydrous tetraalkylammonium salt, which is then heated in anhydrous solvents, e.g., DMF, DMSO, nitromethane, pyridine, and aliphatic and aromatic hydrocarbons, preferably lower aliphatic alcohols, at from 50° C to boiling temperature.

In route C, a compound of the formula IX ($R^1$ denoting hydrogen or tertiary alkyl and R denoting hydrogen or low-molecular-weight alkyl) is expediently cyclized by heating it without solvent and in the presence or absence of solid catalysts such as metal oxides, e.g., thorium(IV) oxide and aluminum oxide, mineral salts such as sulfides, tertiary or secondary calcium phosphate, aluminum phosphate, boron phosphate, acidic ion exchangers and metals, the thiophene saccharine being obtained in the form of a sublimate, or by heating (preferably refluxing) it in a high-boiling solvent which is inert under the reaction conditions, e.g., toluene, xylene, dimethyl sulfone and higher gasoline fractions, and in the presence of Lewis acids such as phosphorus pentoxide and aluminum chloride, acids such as sulfuric acid, polyphosphoric acid and arylsulfonic acids, sulfonated ion exchangers or $PCl_5$. The cyclization method which is particularly preferred is heating with polyphosphoric acid. Similar results are obtained by heating the sulfamoylthiophenecarboxylic acids with an agent which can convert the acid into the chloride, e.g., thionyl chloride.

A thiophene carboxylic acid which may be substituted on the sulfamoyl nitrogen is also suitable as a compound of the formula IX. Thus, for instance, thiophene-3-sulfonyl chloride may be converted into N-tert-butylthiophene-3-sulfonamide, from which the 3-(N-tert-butylsulfamoyl)-thiophene-2-carboxylic acid may be obtained by reaction with n-butyllithium. This thiophenecarboxylic acid is then cyclized in the manner described above.

The intermediate compounds of the formulae V to IX and 4-chlorothiophene-3-carboxylic acid are, as far as can be determined, new compounds; of particular importance are the chlorosulfonylthiophenecarboxylic chlorides X. The corresponding bromides may be prepared analogously and are also suitable for further reaction as described above.

Of similar importance are the esters of chlorosulfonylthiophenecarboxylic acid, particularly those with alcohols of 1 to 4 carbons, which are most suitable starting materials for the manufacture of the new thiophene saccharines.

The new thieno saccharines of the formulae I, II and III are acidic compounds which are used as sweeteners as such or particularly in the form of their non-toxic salts. The salts may be prepared from compounds of the formulae I to III by conventional methods by reaction with suitable organic or inorganic bases, preferably alkali metal hydroxides such as sodium hydroxide and potassium hydroxide, and alkaline earth metal oxides such as calcium hydroxide.

Of the new thieno saccharines, 2,3-dihydro-3-oxo-thieno-[3,5-d]-isothiazole-1,1-dioxide has the greatest sweetening power; it is about 1,000 times sweeter than cane sugar and thus about twice as sweet as saccharine.

The isomers II and III are somewhat less sweet than saccharine (II is 250 times, and III 350 times sweeter than cane sugar) but all three isomers are with respect to taste far superior in the opinion of a large number of taste experts to saccharine, one of the reasons being the absence of any bitter taste; they can as regards quality of taste only be compared with cyclamate, known worldwide as a sweetening agent, but which has inferior sweetening power. Moreover, the compounds of the invention are non-toxic, which makes them particularly suitable for use as artificial sweeteners, e.g., for flavoring foods and beverages and for improving the taste of drugs. As a result of their great sweetening power and their lack of nutritional value, the compounds obtained in accordance with the invention are particularly valuable for sweetening the food of diabetics and for persons tending to obesity or suffering from intestinal disorders. The compounds may also be used as additives to animal feeds.

EXAMPLE 1

2,3-DIHYDRO-3-OXOTHIENO-[3,4-D]-ISOTHIAZOLE-1,1-DIOXIDE 2.14 g of methyl 4-sulfamoylthiophene-3-carboxylate (IX) and 10.2 ml of 1N methanolic sodium methylate solution are refluxed for 18 hours. The methanol is then evaporated off, the residue is taken up in water and bicarbonate, and the aqueous phase is extracted with methylene chloride and acidified with concentrated hydrochloric acid, the desired compound (I) precipitating out. The crystals are suction filtered and recrystallized from water. Melting point: 258° C (sublimes from 200° C); yield: 80%.

The starting material may be prepared as follows. 25 g of the art compound methyl 3-ketothiophane-4-carboxylate dissolved in a small amount of absolute carbon tetrachloride is dripped over a period of 2 hours into a boiling solution of 100 g of phosphorus pentachloride in 250 ml of absolute carbon tetrachloride. The mixture is then refluxed for 15 hours until no more HCl evolves, and is subsequently evaporated at subatmospheric pressure, the major portion of the phosphorus chlorides being thus expelled. The residue is stirred with ice water for 1 hour, the organic phase is separated, the aqueous phase is again extracted with methylene chloride, and the combined organic phases are dried with sodium sulfate and evaporated. The brown oil which remains, 4-chlorothiophene-3-carboxylic chloride, is heated in 2N aqueous caustic soda solution at 50° C until a homogeneous brown solution forms. This solution is extracted with methylene chloride and acidified with concentrated HCl, and the precipitated crystals of crude 4-chlorothiophene-3-carboxylic acid (IV) are suction filtered. To purify the crystals they are dissolved in bicarbonate and reprecipitated with concentrated hydrochloric acid; the compound may be recrystallized from water. Melting point: 164° C; yield: 23%.

8.6 g of 4-chlorothiophene-3-carboxylic acid (IV) is dissolved in 23 ml of water containing 2.1 g of sodium hydroxide in a glass autoclave; a solution of 5.6 g of sodium hydrogen sulfite in 16 ml of water is added and the solution made just alkaline with 30% caustic soda solution. 0.43 g of copper(I) chloride is then added and the mixture heated for 16 hours at 140° to 142° C. After the mixture has cooled the red copper(I) oxide is suction filtered and the filtrate acidified with 7 ml of concentrated HCl, unreacted starting material precipitates out and is removed by extraction with methylene chloride. 12 g of potassium chloride is added to the acidic solution while it is being heated; after cooling to 0° C the potassium salt of 4-sulfothiophene-3-carboxylic acid (V) separates out in the form of colorless crystals; yield: 80%.

ULTIMATE ANALYSIS

| Ultimate analysis | C | H |
|---|---|---|
| Calc.: | 24.28 | 1.22 |
| Found: | 24.28 | 1.21 |

8.2 g of the potassium salt of 4-sulfothiophene-3-carboxylic acid (V) is dissolved in 50 ml of water and this solution is allowed to flow through an ion exchanger column (strongly acidic) laden with protons; rinsing water is passed through until the pH of the solution leaving the exchanger is 5. The solution is evaporated to dryness in vacuo and the crystalline residue, 4-sulfothiophene-3-carboxylic acid (VI), is recrystallized from a small amount of water; melting point: 154° C; yield: 95%.

7.6 g of 4-sulfothiophene-3-carboxylic acid (VI) is dissolved in 140 ml of absolute methanol and 65 ml of absolute chloroform and the mixture is refluxed, the water of reaction being distilled off in a packed column (lm) as a ternary azeotrope (chloroform, methanol, water) (esterification takes place autocatalytically by the sulfo group). The mixture is evaporated at subatmospheric pressure, 100 ml of chloroform is added to the residue to remove traces of methanol, and the mixture is then evaporated at atmospheric pressure. The brown oil which remains, methyl 4-sulfothiophene-3-carboxylate (VII), crystallizes immediately after cooling. The crystals are, however, hygroscopic and deliquesce so quickly that accurate determination of the melting point in accordance with Kofler is not possible; yield: 100%.

7.4 g of crude methyl 4-sulfothiophene-3-carboxylate (VII) is dissolved in 50 ml of thionyl chloride and the mixture is refluxed for 16 hours. It is then evaporated to dryness at subatmosperic pressure and the pale yellow oil which remains, methyl 4-chlorosulfonylthiophene-3-carboxylate (VIII), is crystallized with petroleum ether. Melting point (after recrystallization from petroleum ether): 71° C; yield: 94%.

4 g of methyl 4-chlorosulfonylthiophene-3-carboxylate (VIII) is dissolved in 50 ml of absolute chloroform; at room temperature, ammonia is passed in until the mixture has an alkaline reaction. The mixture is stirred for a further 30 minutes, the ammonium chloride is extracted with water, and the organic phase is dried and evaporated. The crystalline residue, methyl 4-sulfamoylthiophene-3-carboxylate (IX; $R^1$=H), is recrystallized from ethanol; melting point: 128° C; yeild: 85%.

EXMPLE 2

1.0 g of 4-sulfamoylthiophene-3-carboxylic acid (IX; $R^1$ = H, R = H) is stirred into 15 ml of polyphosphoric acid and the mixture is heated on a water bath for 1 hour. The mixture is then poured on to ice and the crystals which precipitate, 2,3-dihydro-3-oxothieno-[3,4-d]-isothiazole-1,1-dioxide (I), are filtered off and recrystallized from water, yield: 60%.

The starting material may be prepared as follows.

2.0 g of methyl 4-sulfamoylthiophene-3-carboxylate (IX) is dissolved in 20 ml of 2N NaOH, the solution is heated on a water bath for 15 minutes and then acidified with concentrated hydrochloric acid, and the colorless crystals which precipitate, 4-sulfamoylthiophene-3-carboxylic acid (IX; $R^1$=H, $R^2$=H), are suction filtered and recrystallized from water; melting point: 215° to 216° C; yield: 95%.

EXAMPLE 3

MONOPOTASSIUM SALT OF 4-SULFOTHIOPHENE 3-CARBOXYLIC ACID (V)

In an autoclave, 60 g (0.37 mole) of 4-chlorothiophene-3-carboxylic acid (IV) and 14.7 g (0.37 mole) of NaOH are dissolved in 160 ml of water; a solution of 40 g (0.384 mole) of anhydrous $NaHSO_3$ in 110 ml of water is added and the solution is made just alkaline (pH ≙ 7.5) with 30% aqueous caustic soda solution. 3 g of copper(I) chloride is then added and the mixture heated for 16 hours at 143°C. After the mixture has cooled, red $Cu_2O$ (sometimes mixed with large portions of black copper sulfide) is filtered off and the residue acidified with 50 ml of concentrated hydrochloric acid at 40° C. Unreacted IV is precipitated and can be removed by suction filtration. 80 g of potassium chloride is added to the acidic solution while it is being heated; after cooling, V separates out as colorless cubic crystals which, after cooling to 5° C overnight, are filtered without rinsing and boiled twice, each time with 300 ml of acetone, to remove any starting material (IV) which may remain. Yield: 68 g (85%, taking unreacted starting material (7 g) into account).

4-CHLOROSULFONYLTHIOPHENE-3-CARBOXYLIC CHLORIDE (X)

94.6 g (0.384 mole) of the monopotassium salt of 4-sulfothiophene-3-carboxylic acid (V) is suspended in 390 ml of $POCl_3$; while stirring, 160.8 g (0.768 mole) of $PCl_5$ is added (accompanied by vigorous evolution of HCl). The mixture is then heated for 3 hours on a water bath while stirring and then cooled to room temperature, inorganic salts are filtered off and the $POCl_3$ is distilled off, as far as possible, at subatmospheric pressure. The residue is dissolved in 400 ml of dry chloroform to remove any inorganic salts which may still be present, filtered and evaporated. The residue crystallizes upon cooling and may be used in the next stage without further purification; melting point: 78° to 79° C; yield: 90.8 g (96.5%).

METHYL 4-CHLOROSULFONYLTHIOPHENE-3-CARBOXYLATE (VIII)

44.1 g (0.18 mole) of 4-chlorosulfonylthiophene-3-carboxylic chloride (X) is dissolved in 450 ml of absolute chloroform; 9.6 g (0.3 mole) of absolute methanol is added and the mixture refluxed for 9 hours (until no more HCl evolves). The mixture is then evaporated to dryness in vacuo at subatmospheric pressure, the residue crystallizing out. The crude product may be used in the next stage. Melting point 71° C; yield: 39.9 g (92%).

METHYL 4-SULFAMOYLTHIOPHENE-3-CARBOXYLATE (IX; R¹=H; R=CH₃)

39.9 g (0.166 mole) of methyl 4-chlorosulfonylthiophene-3-carboxylate (VIII) is dissolved in 400 ml of absolute chloroform; ammonia is passed in at room temperature until the mixture has an alkaline reaction. After the mixture has been stirred for a further 3 hours (care being taken that the solution remains alkaline) it is extracted with water and the organic phase is dried and evaporated. The crystalline residue can be recrystallized from ethanol; however, for further use, digestion with ether is sufficient.

Melting point: 128° C; yield: 31.6 g (86%).

2,3-dihydro-3-oxothieno-[3,4-d]-isothiazole-1,1-dioxide (I)

31.6 g (0.143 mole) of methyl 4-sulfamoylthiophene-3-carboxylate (IX; R¹=H; R=CH₃) is refluxed for 20 hours in 150 ml of 1N methanolic sodium methylate solution. The methanol is evaporated, the residue taken up in water, and the aqueous phase extracted with methylene chloride and acidified with concentrated hydrochloric acid; the product precipitates as crystals. It may be recrystallized from water or ethanol.

Melting point: 258°C; yield: 21.1 g (78%).

EXAMPLE 4

4-SULFAMOYLTHIOPHENE-3-CARBOXAMIDE (XI)

While stirring and at room temperature, dry ammonia gas is passed into a solution of 5 g (20.4 mmoles) of 4-chlorosulfonylthiophene-3-carboxylic chloride (X) in 50 ml of dry chloroform; the temperature rises to 50°C and a colorless precipitate (XI + NH₄Cl) settles out. Ammonia continues to be passed in until the solution shows an alkaline reaction (about 150 minutes) with a moistened pH paper. The precipitate is suction filtered and suspended in 50 ml of methanol, 3.5 g of sodium bicarbonate is added and the mixture is refluxed for 15 minutes (until no more NH₃ evolves). After the mixture has cooled, the sodium chloride which has formed is filtered off and the filtrate concentrated to 10 ml, whereupon XI crystallizes out. The crude product is recrystallized from methanol.

Melting point: 218°–219° C; yield: 1.7 g (40%).

2,3-dihydro-3-oxothieno-[3,4,-d[-isothiazole-1,1-dioxide (I)

In a bomb, 0.41 g (2 mmoles) of 4-sulfamoylthiophene-3-carboxamide (XI) is heated in 8 ml of 1N methanolic sodium methylate solution for 16 hours at 120° C. After the mixture has cooled, the alcohol is evaporated off and the residue is dissolved in water and extracted with methylene chloride. The alkaline aqueous phase is acidified with concentrated hydrochloric acid and the precipitate is filtered off. The crude product is recrystallized from water with the addition of a small amount of activated carbon.

Melting point: 258° C; yield: 0.27 g (71%).

EXAMPLE 5

3-CHLOROTHIOPHENE-2-CARBOXYLIC ACID (IV)

14.5 liters of absolute carbon tetrachloride (refluxed for 1 hour with 500 g of P₂O₅ and then distilled) is placed in a 25 liter apparatus equipped with stirrer, dropping funnel, drainage cock and reflux condenser with gas outlet; while stirring, 2,200 g (10.05 moles) of PCl₅ is added. Upon refluxing the mixture the PCl₅ goes into solution (a small amount of PCl₅ settles in the drainage cock). 660 g (4.18 moles) of methyl 3-hydroxythiophene-2-carboxylate (prepared as described in German Pat. No. 1,020,641) dissolved in 2 liters of absolute carbon tetrachloride is allowed to flow at a just continuous rate over a period of 4 hours into the boiling solution (vigorous evolution of HCl).

The yellow solution is then refluxed for a further 15 hours. Subsequently, 12 liters of carbon tetrachloride is distilled off over a period of 2 hours. After the concentrated solution has been cooled to 40° C it is allowed to drain through the cock. 2 liters of water and 4 kg of ice are now placed in the apparatus. While stirring, the organic phase is quickly run in to hydrolyze the phosphoroxy chloride; the temperature is kept at −2° C by gradual addition of a total of 2 kg of ice. While stirring rapidly, the temperature is kept for 30 minutes at +2° C and for a further 90 minutes at +5° C by cooling with a total of 5 kg of dry ice introduced directly into the solution. The heavier organic phase, which now only contains the acid chloride of IV, is drained off through the cock. The apparatus is cleaned, 12 liters of water is introduced and heated to 90° C and the organic phase is dripped in over a period of 2 hours in such a way that the carbon tetrachloride distills off azeotropically with water at the same rate. A dark brown oily impurity which still contains acid chloride settles out in the cock. The hot aqueous solution of the carboxylic acid is transferred through the cock into an enamel vessel in which it is once again boiled and cooled overnight to +5° C. The needle-shaped crystals which precipitate out are interspersed with a dark brown tar. They are mixed with 320 g of sodium hydrogen carbonate, the mixture is dissolved while boiling in 5 liters of water, the solution is cooled to 80° C and the tar settling out on the surface is skimmed off. The solution is then cooled to 40° C, 100 g of activated carbon is stirred in, and suction filtration carried out. The filtrate is made strongly acid with about 750 ml of concentrated hydrochloric acid, whereupon IV precipitates out as a thick crystal slurry. After cooling the slurry to 10° C it is suction filtered and the pale brown crystals are dried at 110° C in a through-circulation drier. The product may be used in the next stage without further purification.

Melting point: 186° C; yield: 272 g (40%).

MONOPOTASSIUM SALT OF 3-SULFOTHIOPHENE-2-CARBOXYLIC ACID (V)

60 g (0.37 mole) of 3-chlorothiophene-2-carboxylic acid (IV) dissolved in 160 ml of water and 14.7 g (0.37 mole) of NaOH is placed in an autoclave. A solution of 40 g (0.384 mole) of anhydrous NaHSO₃ in 110 ml of water is added and the solution is made just alkaline (pH of about 7.5) with 30% caustic soda solution. After the addition of 3 g of copper (I) chloride the mixture is heated for 16 hours at 143° C. After the mixture has cooled the red Cu₂O (sometimes mingled to a considerable extent with black copper sulfide) is filtered off and the residue acidified with 50 ml of concentrated hydrochloric acid at 40° C. Unreacted IV precipitates out and can be suction filtered 80 g of potassium chloride is added to the acidic solution while it is being heated; upon cooling, V separates out as colorless cubic crystals. After they have been cooled to 5° C overnight they are filtered without rinsing and boiled twice, each time with 300 ml of acetone, to remove any starting material (IV) which may remain.

Yield: 68 g (85%, taking unreacted starting material (7g) into account).

3-CHLOROSULFONYLTHIOPHENE-2-CARBOXYLIC CHLORIDE (X)

50 g (0.203 mole) of the monopotassium salt of 3-sulfothiophene-2-carboxylic acid (V) is suspended in 250 ml of $POCl_3$; while stirring, 85 g (0.406 mole) of $PCl_5$ is added (vigorous evolution of HCl). The mixture is heated with stirring on a water bath for 90 minutes and then cooled to room temperature; inorganic salts are suction filtered and the $POCl_3$ distilled off, as far as possible, in vacuo. To remove any inorganic salts which may still be present, the oily residue is dissolved in 400 ml of dry chloroform, filtered and evaporated. The oily residue crystallizes upon cooling and is used in the next stage without further purification.

Melting point: 42°–43° C; yield: 48 g (96.5%).

METHYL 3-CHLOROSULFONYLTHIOPHENE-2-CARBOXYLATE (VIII)

48 g (0.196 mole) of 3-chlorosulfonylthiophene-2-carboxylic chloride (X) is dissolved in 500 ml of absolute chloroform; 9.6 g (0.3 mole) of absolute methanol is added and the mixture refluxed for 3 hours (until no more HCl evolves). The mixture is then evaporated to dryness at subatmospheric pressure, whereupon the residue — pure VIII — crystallizes out. The crude product may be in the next stage.

Melting point: 60°–63° C; yield: 43.5 g (92%).

METHYL 3-SULFAMOYLTHIOPHENE-2-CARBOXYLATE (IX)

43.5 g (0.181 mole) of methyl 3-chlorosulfonylthiophene-2-carboxylate (VIII) is dissolved in 450 ml of absolute chloroform; ammonia is passed in at room temperature until the mixture has an alkaline reaction. After stirring the solution for a further 3 hours at room temperature (care being taken to keep the solution alkaline) it is extracted with water and the organic phase is dried and evaporated. The crystalline residue may be recrystallized from ethanol; however, for further reaction digestion with ether is sufficient.

Melting point: 121°–122° C; yield: 32 g (80%).

2,3-DIHYDRO-3-oxothieno-[2,3-d]-ISOTHIAZOLE-1,1-DIOXIDE (II)

32 g (0.145 mole) of methyl 3-sulfamoylthiophene-2-carboxylate (IX) in 145 ml of 1N methanolic sodium methylate solution is refluxed for 18 hours. The methanol is then evaporated off, the residue is taken up in water and a small amount of sodium bicarbonate, and the aqueous phase is extracted with methylene chloride and acidified with concentrated hydrochloric acid, whereupon the product precipitates as crystals which can be reprecipitated from water or ethanol.

Melting point: 220° – 222° C; yield: 20.6 g (75%).

EXAMPLE 6

2.14 g of methyl 3-sulfamoylthiophene-2-carboxylate (IX) in 10.2 ml of 1N methanolic sodium methylate solution is refluxed for 18 hours. The methanol is then evaporated, the residue is taken up in water and bicarbonate, and the aqueous phase is extracted with methylene chloride and acidified with concentrated hydrochloric acid. The crystals of 2,3-dihydro-3-oxothieno-[2,3-d]-isothiazole-1,1-dioxide (II) which precipitate out are suction filtered and recrystallized from water.

Melting point: 220°–222° C (sublimes at 180° C); yield: 75%

2,3-DIHYDRO-3-OXOTHIENO-[2,3-d]-ISOTHIAZOLE-1,1-DIOXIDE VIA THE ACID CHLORIDE 1.0 g of 3-sulfamoylthiophene-2-carboxylic acid is suspended in 20 ml of thionyl chloride and brought to the boil under reflux. The carboxylic acid goes into solution at the rate at which the chloride is formed (in about 20 min.). 2,3-dihydro-3-oxothieno-[2,3-d]-isothiazole-1,1-dioxide is then formed from this chloride through heating under reflux for a further 24 hours. The excess $SOCl_2$ is then evaporated in vacuo, and the crystalline residue is washed with water and recrystallized from or ethanol.

Yield: 0.7 g (77%).

The starting material may be prepared as follows.

8.6 g of the art 3-chlorothiophene-2-carboxylic acid (IV) is dissolved in 23 ml of water containing 2.1 g of sodium hydroxide in a glass autoclave; a solution of 5.6 g of sodium hydrogen sulfite in 16 ml of water is added and the solution made just alkaline with 30% caustic soda solution. 0.43 g of copper (I) chloride is then added and the mixture heated for 16 hours at 140° to 142° C. After the mixture has cooled the red copper (I) oxide is suction filtered and the filtrate acidified with 7 ml of concentrated HCl; unreacted starting material precipitates out and is removed by extraction with methylene chloride. 12 g of potassium chloride is added to the acidic solution while it is being heated; after cooling to 0° C the potassium salt of 3-sulfothiophene-2-carboxylic acid (V) separates out in the form of colorless crystals; yield: 76%.

ULTIMATE ANALYSIS

| Ultimate analysis | C | H |
|---|---|---|
| Calc.: | 24.38 | 1.23 |
| Found: | 24.37 | 1.24 |

8.2 g of the potassium salt of 3-sulfothiophene-2-carboxylic acid (V) is dissolved in 50 ml of water and this solution is allowed to flow through an ion exchanger column (strongly acidic) laden with protons; rinsing water is passed through until the pH of the solution leaving the exchanger is 5. The solution is evaporated to dryness in vacuo and the crystalline residue, 3-sulfothiophene-2-carboxylic acid (VI), is recrystallized from a small amount of water; melting point: 107°–110° C; yield: 88%.

7.6 g of 3-sulfothiophene-2-carboxylic acid (VI) is dissolved in 140 ml of absolute methanol and 65 ml of absolute chloroform and the mixture is refluxed, the water of reaction being distilled off in a packed column (1 m) as a ternary azeotrope (chloroform, methanol, water) (esterification takes place autocatalytically by the sulfo group). The mixture is evaporated at subatmospheric pressure, 100 ml of chloroform is added to the residue to remove traces of methanol, and the mixture is then evaporated at atmospheric pressure. The brown oil which remains, methyl 3-sulfothiophene-2-carboxylate (VII), crystallizes immediately after cooling. The crystals are, however, hygroscopic and deliquesce so quickly that accurate determination of the melting point in accordance with Kofler is not possible; yield: 91%.

7.4 g of crude methyl 4-sulfothiophene-3-carboxylate (VII) is dissolved in 50 ml of thionyl chloride and the mixture is refluxed for 16 hours. It is then evaporated to dryness at subatmospheric pressure and the pale yellow oil which remains, methyl 3-chlorosulfonylthiophene-2-carboxylate (VIII), is crystallized with petroleum ether.

Melting point: 59°–63° C; yield: 100%.

4 g of methyl 3-chlorosulfonylthiophene-2-carboxylate (VIII) dissolved dissoved in 50 ml of absolute chloroform; at room temperature, ammonia is passed in until the mixture has an alkaline reaction. The mixture is stirred for a further 30 minutes, the ammonium chloride is extracted with water, and the organic phase is dried and evaporated. The crystalline residue, methyl 3-sulfamoylthiophene-2-carboxylate (IX), is recrystallized from ethanol; melting point: 121°–122.5° C; yield: 65%.

EXAMPLE 7

10 g of 3-sulfamoylthiophene-2-carboxylic acid (IX; R=H) is stirred into 15 ml of polyphosphoric acid and the mixture is heated on a water bath for 1 hour. The mixture is then poured on to ice and the crystals which precipitate, 2,3-dihydro-3-oxothieno- [2,3-d]-isothiazole-1,1-dioxide (II), are filtered off and recrystallized from water; yield: 60%.

The starting material may be prepared as follows.

2.0 g of methyl 3-sulfamoylthiophene-2-carboxylate (IX) is dissolved in 20 ml of 2N NaOH, the solution is heated on a water bath for 15 minutes and then acidified with concentrated hydrochloric acid, and the colorless crystals which precipitate, 3-sulfamoylthiophene-2-carboxylic acid, are suction filtered and recrystallized from water; melting point: 203° to 205° C; yield: 95%.

EXAMPLE 8 a. 18 g of 3-(N-tert-butylsulfamoyl)-thiophene-2-carboxylic acid (IX; R=H; R$^1$=tert-butyl) in 180 ml of polyphosphoric acid is heated, with continuous stirring, on a boiling water bath for 20 minutes. The viscous mixture is then poured hot (while still being stirred) on to about 600 g of finely crushed ice, whereupon the desired product precipitates out in the form of crystals. The solid is suction filtered and the filtrate is extracted twice, each time with 200 ml of ether, dried over sodium sulfate, evaporated and combined with the major portion. A total of 8 g of 2,3-dihydrothieno-[2,3-d]-isothiazol- 2-one-1,1-dioxide (II) is obtained.

b. 3-(N-tert-butylsulfamoyl)-thiophene-2-carboxylic acid is heated at 200° C (1 mm); 2,3-dihydrothieno-[2,3-d]-isothiazol-3-one-1,1-dioxide is obtained as a sublimate.

Yield: 30%.

The starting material may be prepared as follows.

At 0° C and while stirring, a solution of 33.6 g of thiophene- 3-sulfonyl chloride in 150 ml of absolute chloroform is slowly dripped into a solution of 49 g of tert-butylamine in 120 ml of absolute chloroform. The mixture is then stirred for 1 hour at room temperature and refluxed for a further hour. The suspension is cooled and extracted thoroughly, three times with 300 ml of 3N hydrochloric acid and twice with 300 ml of water. The aqueous phase is extracted with chloroform and the combined organic phases are dried over sodium sulfate and evaporated, N-tert-butylthiophene-3-sulfonamide crystallizing out.

Melting point (cyclohexane): 103°–104° C; yield: 80%.

29 g of N-tert-butylthiophene-3-sulfonamide is dissolved in 300 ml of absolute ether; while stirring this solution, 197 ml of ethereal n-butyllithium solution containing a total of 0.216 mole of n-butyllithium is slowly dripped in under a nitrogen blanket. The temperature rises to about 30° C and a white suspension forms which turns into a clear yellow solution toward completion of the addition. The nitrogen supply is then cut and the solution is refluxed for 2½ hours. After the solution cooled, dry carbon dioxide is passed in over a period of 30 minutes while stirring. 1 liter of water is then added to the reaction mixture, the clear ether phase is removed and discarded, and the aqueous phase is acidified with concentrated hydrochloric acid and extracted twice, each time with 400 ml of methylene chloride. The combined methylene chloride phases are dried over sodium sulfate and evaporated; 3-(N-tert-butylsulfamoyl)-thiophene-2-carboxylic acid crystallizes out.

Melting point: 161°–163° C; yield: 50%.

EXAMPLE 9

2,3-DIHYDRO-3-OXOTHIENO-[3,2-d]-ISOTHIAZOLE-1,1-DIOXIDE (III)

1.1 g of methyl 2-sulfamoylthiophene-3-carboxylate (IX; R$^1$=H; R=CH$_3$) is dissolved in 6 ml of 1N methanolic sodium methylate solution and refluxed for 40 hours. The methanol is evaporated, the residue is taken up in water and sodium bicarbonate, and the aqueous phase is extracted with methylene chloride and acidified with concentrated hydrochloric acid, 2,3-dihydro-3-oxothieno-[3,2-d]-isothiazole-1,1-dioxide (III) precipitating out. The crystals are suction filtered and recrystallized from water.

Melting point: 240°–242° C.

The starting material may be prepared as follows.

73 g of the art compound 2,5-dichlorothiophene-3-carboxylic acid is dissolved with heating in a glass autoclave in 160 ml of water containing 14.7 g of sodium hydroxide; a solution of 39.1 g of sodium hydrogen sulfite in 108 ml of water is added and the solution made just alkaline with 30% caustic soda solution. 3 g of copper(I) chloride is then added and the mixture heated for 16 hours at 140° to 142° C. After the mixture has cooled the red copper(I) oxide is suction filtered and the filtrate strongly acidified with concentrated HCl. The mixture is heated to 80° C and 150 g of potassium chloride is added. Upon cooling, the monopotassium salt of 5-chloro-2-sulfothiophene-3-carboxylic acid precipitates out in the form of colorless crystals. It is suction filtered and washed with a small amount of ice-cold water. To remove unreacted starting material the crystals are boiled several times with methylene chloride.

Yield: 31%.

| Ultimate analysis: | C | H |
|---|---|---|
| Calc.: | 21.40 | 0.72 |
| Found: | 21.59 | 0.73 |

14 g of the potassium salt of 5-chloro-2-sulfothiophene-3-carboxylic acid is dissolved in 80 ml of water containing 5.6 g of potassium hydroxide; at room temperature and atmospheric pressure the solution is hydrogenated with 0.9 g of palladium/activated carbon (10% palladium) as catalyst until no more hydrogen is absorbed. The solution containing the dipotassium salt of 2-sulfothiophene-3-carboxylic acid is filtered off from the catalyst and allowed to flow through a proton-laden ion exchanger (strongly acidic); rinsing water is passed through the column until the pH of the solution leaving it is 5. The solution is evaporated to dryness in vacuo and the crystalline residue, 2-sulfothiophene-3-carboxylic acid (VI), is recrystallized from a small amount of water.

Melting point: 118°–121° C; yield: 80%.

10 g of 2-sulfothiophene-3-carboxylic acid (VI) is dissolved in 220 ml of absolute methanol and 110 ml of absolute chloroform and the mixture is refluxed, the water of reaction being distilled off in a packed column (1 m) as a ternary azeotrope (chloroform, methanol, water) (esterification takes place autocatalytically at the sulfo group). The mixture is evaporated in vacuo, 200 ml of chloroform is added to the residue to remove traces of methanol, and the mixture is then evaporated at atmospheric pressure. The colorless oil which remains is methyl 2-sulfothiophene-3-carboxylate (VII).

Yield: 88%.

10.5 g of crude methyl 2-sulfothiophene-3-carboxylate (VII) is dissolved in 250 ml of thionyl chloride and the solution refluxed for 16 hours. It is then evaporated to dryness at subatmospheric pressure and the pale yellow oil which remains, methyl 2-chlorosulfonylthiophene 3-carboxylate (VIII), is crystallized with ether.

Melting point: 51°–54° C; yield: 91%.

5 g of methyl 2-chlorosulfonylthiophene-3-carboxylate (VIII) is dissolved in 50 ml of absolute chloroform, and ammonia passed in at room temperature until the solution has an alkaline reaction. It is stirred for a further 30 minutes, the ammonium chloride is extracted with water, the organic phase is dried and the mixture evaporated. The crystalline residue, methyl 2-sulfamoylthiophene-3-carboxylate (IX, $R^1$=H, R=CH$_3$), is recrystallized from ethanol.

Melting point: 131°–133° C; yield: 66%.

EXAMPLE 10

1.0 g of 2-sulfamoylthiophene-3-carboxylic acid (IX; $R^1$=H, R=H) is stirred into 15 ml of polyphosphoric acid and the mixture is heated for 1 hour on a water bath. The mixture is then poured on to ice and the crystals which precipitate, 2,3-dihydro-3-oxothieno-[3,2-d]-isothiazole-1,1-dioxide (III), are filtered off and recrystallized from water.

Yield: 60%.

The starting material may be prepared as follows.

2.0 g of methyl 2-sulfamoylthiophene-3-carboxylate (IX; $R^1$=H, R=CH$_3$) is dissolved in 20 ml of 2N NaOH and the solution is heated for 15 minutes on a water bath. The solution is then acidified with concentrated hydrochloric acid and the colorless crystals which precipitate, 2-sulfamoylthiophene-3-carboxylic acid (IX; $R^1$=H, R=H), are suction filtered and recrystallized from water.

Melting point: 202°–204° C; yield: 95%.

We claim:

1. Thiophene saccharines of the formulae 2,3-dihydro-3-oxothieno-[3,4-d]-isothiazole-1,1-dioxide

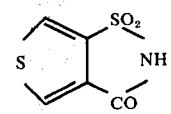   I, 2,3-dihydro-3-oxothieno-[2,3-d]-isothiazole-1,1-dioxide

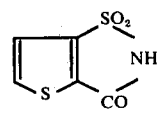   II and and 2,3-dihydro-3-oxothieno-[3,2-d]-isothiazole-1,1-dioxide

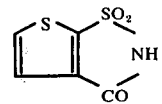   III and their non-toxic water-soluble salts.

2. The sodium salts of thiophene saccharines of the formulae I to III as claimed in claim 1.

3. The potassium salts of thiophene saccharines of the formulae I to III as claimed in claim 1.

4. The calcium salts of thiophene saccharines of the formulae I to III as claimed in claim 1.

5. The ammonium salts of thiophene saccharines of the formulae I to III as claimed in claim 1.

6. 2,3-Dihydro-3-oxothieno-[3,4-d]-isothiazole-1,1-dioxide.

7. 2,3-Dihydro-3-oxothieno-[2,3-d]-isothiazole-1,1-dioxide.

8. 2,3-Dihydro-3-oxothieno-[3,2-d]-isothiazole-1,1-dioxide.

* * * * *